United States Patent [19]
Okigami et al.

[11] Patent Number: 5,743,269
[45] Date of Patent: Apr. 28, 1998

[54] CARDIOTACHOMETER

[75] Inventors: Tomio Okigami, Tokorozawa; Hiroyuki Kihara, Kodaira; Tomomi Murakami, Higashimurayama; Takashi Osa, Sayama, all of Japan

[73] Assignee: Citizen Watch Co. Ltd., Tokyo, Japan

[21] Appl. No.: 737,565

[22] PCT Filed: Mar. 15, 1996

[86] PCT No.: PCT/JP96/00661

§ 371 Date: Nov. 12, 1996

§ 102(e) Date: Nov. 12, 1996

[87] PCT Pub. No.: WO96/29005

PCT Pub. Date: Sep. 26, 1996

[30] Foreign Application Priority Data

Mar. 17, 1995 [JP] Japan .................................. 7-057871
Aug. 9, 1995 [JP] Japan .................................. 7-202971
Aug. 9, 1995 [JP] Japan .................................. 7-202972

[51] Int. Cl.$^6$ ........................................................ A61B 5/04
[52] U.S. Cl. ......................................... 128/706; 128/903
[58] Field of Search ........................... 128/670, 690, 128/706, 707, 779, 784, 903

[56] References Cited

U.S. PATENT DOCUMENTS

| | | | |
|---|---|---|---|
| 3,953,848 | 4/1976 | Dillman et al. | 128/903 |
| 3,972,320 | 8/1976 | Kalman | 128/706 |
| 4,202,350 | 5/1980 | Walton | 128/690 |
| 4,830,021 | 5/1989 | Thornton | 128/707 |
| 5,157,604 | 10/1992 | Axford et al. | 128/706 |

Primary Examiner—William E. Kamm
Attorney, Agent, or Firm—Townsend and Townsend and Crew LLP

[57] ABSTRACT

An improved cardiotachometer comprises a transmitting section and a receiving section. The transmitting section includes a detection circuit for detecting electrocardiographic signals obtained from a pair of electrodes mounted near the heart of a human body. The transmitting section processes and transmits the electrocardiographic data with ID code data to the receiving section in the form of a radio signal. The receiving [section?] compares the transmitted ID code with a stored ID code. If the two codes do not agree, the receiving section does not make any calculations or modify the previous signal. If the two codes agree, a genuine reception has resulted and the receiving section computes a heart rate based on the electrocardiographic data. A display section displays the computed heart rate. The use of the ID code comparison method eliminates erroneous reception of signals generated by noise or interference by the receiving section.

8 Claims, 7 Drawing Sheets

FIG. 7

| ID CODE | INTERVAL DATA | WALKING INTERVAL DATA | NUMBER-OF-STEPS DATA | BATTERY VOLTAGE DROP WARNING DATA | ID CODE |
|---|---|---|---|---|---|

# CARDIOTACHOMETER

BACKGROUND OF THE INVENTION

The present invention relates to a cardiotachometer which detects an electrocardiographic signal, transmits information on cardio-condition by radio, and receives the information by radio to display a heart rate at a distant place.

For example, Japanese Unexamined Utility Model Publication No. 3-5405 discloses a cardiotachometer for observing a heart rate at a distant place. The cardiotachometer includes a transmitting section for detecting an electrocardiographic signal obtained from a pair of electrodes mounted near the heart of a user and transmitting the resultant information by radio, and a compact information device as a receiving section which is incorporated in a wristwatch or the like and can display the heart rate by performing an arithmetic operation based on the received radio signal.

In the above conventional cardiotachometer, the transmitting section transmits a radio signal every time an electrocardiographic signal is detected, and the receiving section receives the signal. That is, the reception timing coincides with the heartbeat timing. When the receiving section erroneously receives various types of noise such as electromagnetic noise caused by the alarm sound emitted at a railway crossing, the reception timing of the noise deviates from the heartbeat timing, and hence an erroneous heart rate is displayed.

SUMMARY OF THE INVENTION

It is an object of the present invention to provide a cardiotachometer which solves the problem in the conventional cardiotachometer and employs an improved communication method for transmitting and receiving sections to be free from the influence of noise.

An arrangement of the present invention comprises a transmitting section and a receiving section. The transmitting section includes a detection circuit for detecting an electrocardiographic signal obtained from a pair of electrodes mounted near the heart of a human body and generating a detection signal, an interval data creating circuit for counting generation intervals of the detection signals with signals of a predetermined period and generating interval data, a serial data creating circuit for converting the interval data into a serial signal and generating a serial data signal, a transmission circuit for modulating the serial data signal and transmitting the signal as a radio signal, and a battery as a power supply. The receiving section includes a reception circuit for receiving and demodulating the radio signal from the transmitting section and generating a reception signal, a data decoding circuit for decoding the reception signal and generating electrocardiographic interval data, a calculation circuit for calculating a heart rate from the electrocardiographic interval data, and a display section for displaying the heart rate.

With the above arrangement even if the reception circuit receives noise or an irrelevant signal, the data decoding circuit cannot properly decode the data since the signal is not pertinent data. Because the data obtained in the previous proper reception is displayed, no erroneous heart rate is displayed.

BRIEF DESCRIPTION OF THE DRAWINGS

FIG. 7 is a view showing an example of the format of a signal to be transmitted from the transmitting section to the receiving section.

DETAILED DESCRIPTION OF THE PREFERRED EMBODIMENTS

A cardiotachometer according to this invention can display information based on a signal other than an electrocardiographic signal (to be referred to as "second information" hereinafter) on a receiving section. For example, this second information includes number of steps per minute taken by a user having a transmitting section mounted thereon, total number of steps, and a warning about a battery voltage drop in the transmitting section.

Figure 1:
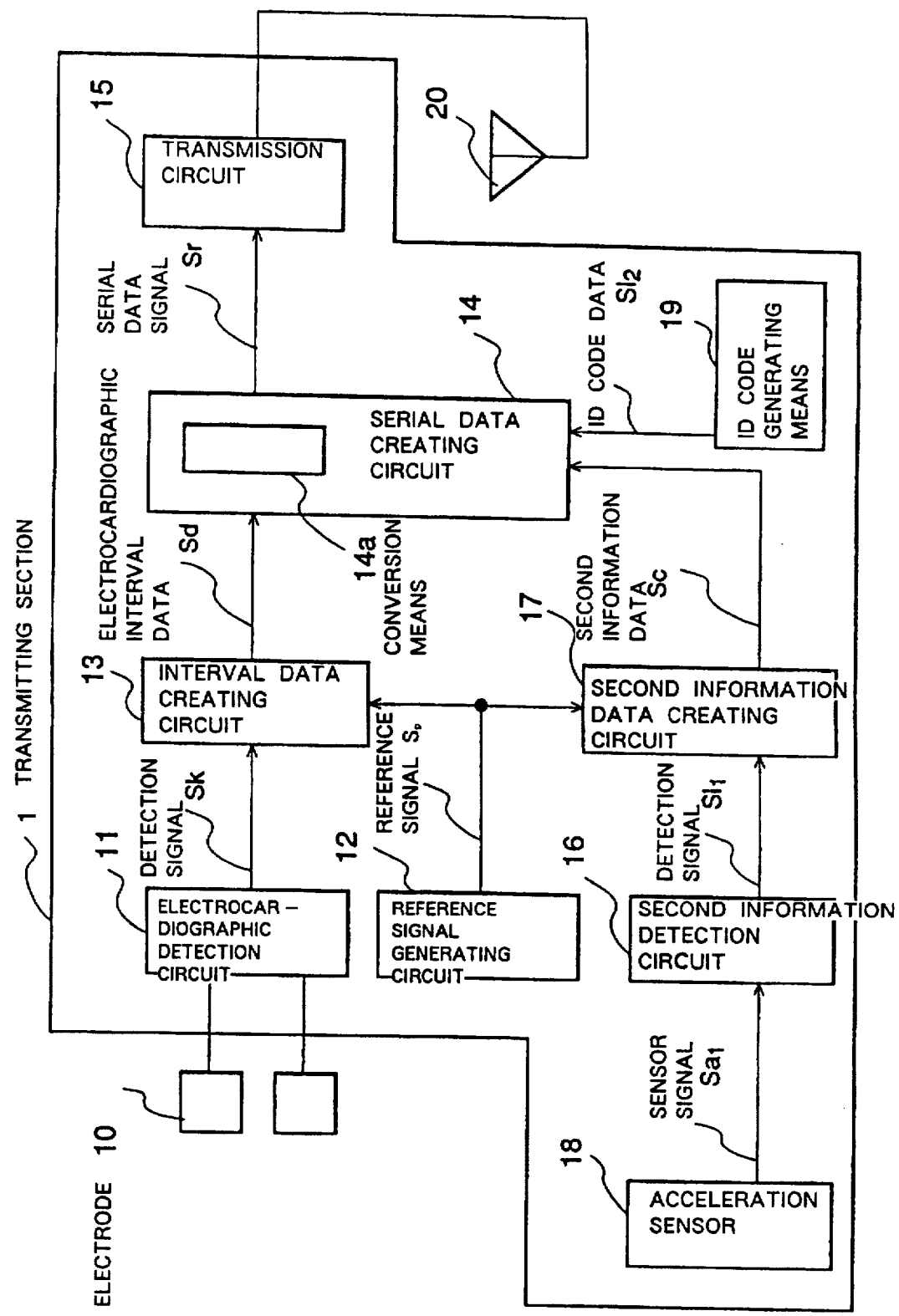
FIG. 1 is a block diagram showing the transmitting section of a cardiotachometer according to an embodiment of the present invention.

Referring to FIG. 1, the second information is assumed to be the walking pitch, i.e. the number of steps per minute.

Electrodes 10 are to be mounted near the heart of a human body. An electrocardiographic detection circuit 11 detects and amplifies an electrocardiographic signal detected by the electrodes 10, and outputs a detection signal Sk as a pulse signal synchronized with the electrocardiographic signal. An interval data creating circuit 13 counts the generation intervals of the detection signals Sk with reference signals Sp output from a reference signal generating circuit 12 to compute a count value. The interval data creating circuit 13 outputs the count value as electrocardiographic interval data Sd to the serial data creating circuit 14.

A second information detection circuit 16 detects a sensor signal $Sa_1$ as an electrical signal based on an acceleration change produced by an acceleration sensor 18. The second information detection circuit 16 amplifies the detected signal and outputs a detection signal $Sl_1$ as a pulse signal synchronized with the sensor signal $Sa_1$. A second information data creating circuit 17 counts the generation intervals of the detection signals $Sl_1$ using the reference signals Sp output from the reference signal generating circuit 12, and outputs the count value as walking pitch data Sc, which is second information data, to the serial data creating circuit 14.

An ID code generating means 19 generates a predetermined ID code. A serial data creating circuit 14 converts the ID code into ID code data $Sl_2$, which can be processed, and outputs the data to the serial data creating circuit 14.

The serial data creating circuit 14 links the electrocardiographic interval data Sd, the second information data Sc, and the ID code data $Sl_2$ by using a conversion means 14a, converts the resultant data into serial data, and outputs a serial data signal Sr every Tj seconds to a transmission circuit 15. Every time a serial data signal Sr is input, the transmission circuit 15 modulates the serial data signal Sr and transmits it as a radio signal through an antenna 20 to the receiving section.

In this embodiment, the serial data signal Sr is transmitted as a radio signal every Tj seconds. Tj may be any number, but desirably allows a proper response to a variation in heartbeat or walking pitch (e.g. one, five, or 10 seconds).

Figure 2:
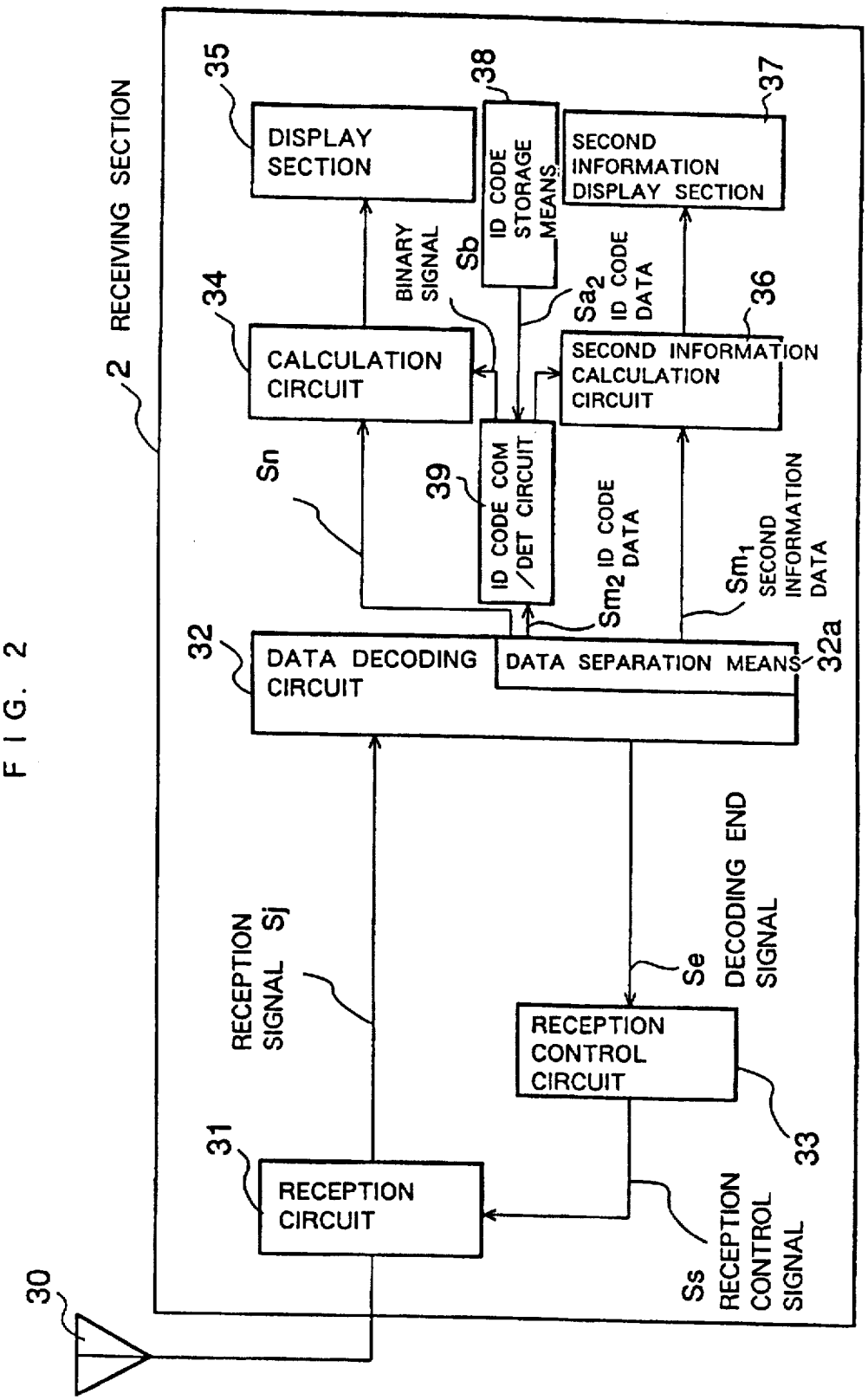
FIG. 2 is a block diagram showing the receiving section of the cardiotachometer according to the embodiment of the present invention.

FIG. 2 is a block diagram showing the receiving section 2 of the cardiotachometer according to the embodiment of the present invention.

A reception circuit 31 amplifies, detects, and demodulates the radio signal received from the transmitting section 1 through an antenna 30, and outputs a reception signal Sj to a data decoding circuit 32. The reception circuit 31 is deactivated upon reception of a reception control signal Ss from a reception control circuit 33. The reception signal Sj is identical to the serial data signal Sr from the transmitting section 1.

The data decoding circuit 32 decodes the reception signal Sj, and separates and outputs electrocardiographic interval data Sn to a calculation circuit 34, second information data $Sm_1$ to a second information calculation circuit 36, and ID code data $Sm_2$ to an ID code comparison/determination circuit 39 through a data separation means 32a. The electrocardiographic interval data Sn is identical to the electrocardiographic interval data Sd from the transmitting section 1. The second information data $Sm_1$ is identical to the detection signal $Sl_1$ from the transmitting section 1. The ID code data $Sm_2$ is identical to the ID code data $Sl_2$ from the transmitting section 1. When the data decoding circuit 32 properly decodes the electrocardiographic interval data Sn, the second information data $Sm_1$, and the ID code data $Sm_2$, the circuit 32 outputs a decoding end signal Se as a one-shot signal to the reception control circuit 33. Upon reception of the decoding end signal Se, the reception control circuit 33 outputs the reception control signal Ss as a pulse signal having a constant width. The pulse width of the reception control signal Ss is shorter than the interval (Tj seconds) of radio signals transmitted from the transmitting section 1. The decoding end signal Se and the reception control signal Ss are used to reduce the power consumption. This operation will be described later.

An ID code storage means 38 stores the ID code unique to each cardiotachometer. The value of this code is equal to that of the ID code produced by the ID code generating means 19 on the transmission side. The ID code storage means 38 outputs the stored ID code data as an electrical signal $Sa_2$.

The ID code comparison/determination circuit 39 compares the ID code data $Sm_2$ decoded by the data decoding circuit 32 and the electrical signal $Sa_2$ output from the ID code storage means 38, and determines and outputs a binary signal Sb as the comparison/determination result to a calculation circuit 34 and a second information calculation circuit 36.

The calculation circuit 34 calculates the electrocardiographic interval data Sn, converts the data into a heart rate, and displays the heart rate on a display section 35. The second information calculation circuit 36 calculates the second information data $Sm_1$, converts the data into data which can be displayed, e.g. a walking pitch, and displays it on a second information display section 37.

The operation of the cardiotachometer of the present invention having the above arrangement will be described.

The operation of the transmitting section 1 will be described first with reference to FIG. 1.

An electrocardiographic signal detected by the electrodes 10 is converted into a detection signal Sk by the electrocardiographic detection circuit 11. The interval data creating circuit 13 counts the intervals of the detection signals Sk with reference signals Sp output from the reference signal generating circuit 12. Assume that the reference signal Sp has a frequency of 600 Hz. If, for example, the heart rate is 80, the intervals of the detection signals Sk are 750 ms, and the count value is 450.

When the acceleration sensor 18 detects a periodic acceleration change which occurs during a walk, the second information detection circuit 16 converts the detected change into a sensor signal $Sa_1$. The sensor signal $Sa_1$ is amplified to output a second information detection signal $Sl_1$ in synchronism with the walking pitch. The second information data creating circuit 17 counts the intervals of the second information detection signals $Sl_1$ with the reference signals Sp output from the reference signal generating circuit 12. If the pitch count per minute is 120, the intervals of the second information detection signals $Sl_1$ are 500 ms, and the count value is 300.

The count value "450" obtained by the interval data creating circuit 13 is sent as electrocardiographic interval data Sd to the serial data creating circuit 14. The count value "300" obtained by the second information detection circuit 16 is sent as second information data Sc to the serial data creating circuit 14.

Assume that the ID code generating means 19 generates an ID code, e.g. "No. 10". The ID code generating means 19 converts this ID code "No. 10" into ID code data $Sl_2$, which is a numerical value "10" and can be processed by the serial data creating circuit 14, and outputs it to the serial data creating circuit 14.

The serial data creating circuit 14 links the electrocardiographic interval data Sd, the second information data Sc, and the ID code data $Sl_2$ in the conversion means 14a, and converts the resultant data into a serial data signal Sr as serial data every Tj seconds. The transmission circuit 15 transmits the serial data signal Sr as a radio signal through the antenna 19.

The serial data signal Sr is transmitted as a radio signal every Tj seconds. In the conventional scheme, since transmission is performed every time a heartbeat is detected, transmission must be performed more than ten times per second. In contrast, transmission in the present scheme is performed for intervals that are substantially more than ten seconds. Therefore, the number of times of transmission per unit time can be greatly decreased, and the power consumption of the transmitting section 1 can be greatly reduced.

The operation of the receiving section 2 will be described next with reference to FIG. 2.

The radio signal transmitted from the transmitting section 1 is input to the reception circuit 31 through the antenna 30. The reception circuit 31 outputs a reception signal Sj. The reception signal Sj is a serial signal, which is decoded into electrocardiographic interval data Sn, second information data $Sm_1$, and ID code data $Sm_2$ by the data decoding circuit 32.

If the value of the electrocardiographic interval data Sd from the transmitting section 1 is 450 as in this example, the value of the electrocardiographic interval data Sn also becomes 450. The value "450" is counted with the intervals of electrocardiographic signals being set to 600 Hz. The calculation circuit 34 therefore calculates 36,000/Sn to obtain the heart rate per minute. This heart rate is displayed on the display section 35. Similarly, if the value of the second information data Sc from the transmitting section 1 is 300, the value of the second information data $Sm_1$ as the walking pitch becomes 300. The value "300" is a value counted with the intervals of electrocardiographic signals being set to 600 Hz. The second information calculation circuit 36 therefore calculates 36,000/Sm$_1$ to obtain the walking pitch per minute. This walking pitch is displayed on the second information display section 37.

The ID code comparison/determination circuit 39 compares an ID code data Sm$_2$ decoded by the data decoding circuit 32 with an electrical signal Sa$_2$ stored in the ID code storage means 38. Since the ID codes of the transmitting section 1 and the receiving section 2 are identical, if reception has succeeded, the ID code data Sm$_2$ and the electrical signal Sa$_2$ should coincide with each other. If they do not coincide with each other, a reception failure has occurred because of interference or the like. In this case, since the electrocardiographic interval data Sn and the second information data Sm$_1$ are unreliable, the calculation result obtained when the previous reception has succeeded should continue to be displayed without performing any arithmetic processing in the calculation circuit 34 and the second information calculation circuit 36. The ID code comparison/determination circuit 39 outputs a binary signal Sb indicating coincidence/noncoincidence as the result of comparison to the calculation circuit 34 and the second information calculation circuit 36. If the binary signal Sb indicates coincidence as the result, the calculation circuit 34 and the second information calculation circuit 36 perform the above calculation and display. If, however, the binary signal Sb indicates noncoincidence as the result, no calculation is performed, and the previous calculation results are kept displayed on the display section 35 and the second information display section 37.

The operation of the reception control circuit 33 will now be described in reference to FIG. 3.

A radio signal is received by the reception circuit 31, and a reception signal Sj is output. The data decoding circuit 32 decodes the reception signal Sj. The data separation means 32a then outputs electrocardiographic interval data Sn, second information data Sm$_1$, and ID code data Sm$_2$. When the decoding operation is properly completed, the data decoding circuit 32 outputs a decoding end signal Se.

Figure 3:
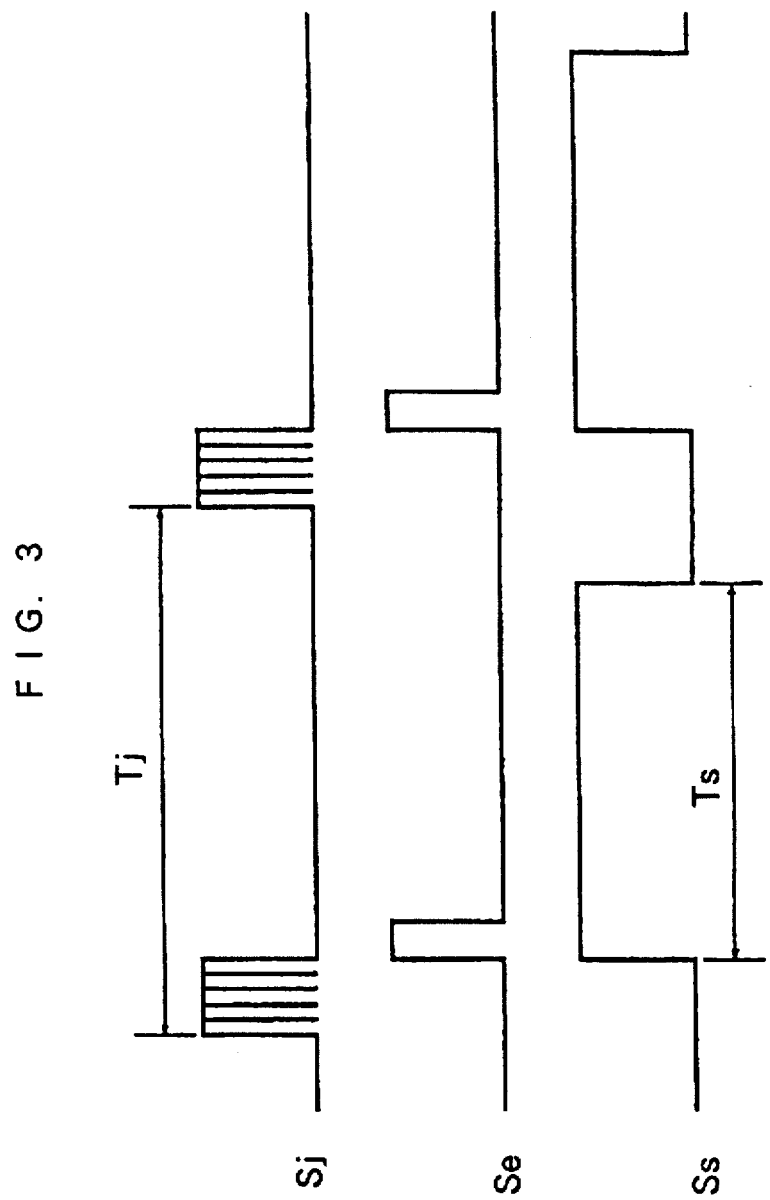
FIG. 3 is a timing chart for illustrating the operation of a reception control circuit.

Upon reception of the decoding end signal Se, the reception control circuit 33 outputs a reception control signal Ss having a pulse width of Ts seconds to stop the operation of the reception circuit 31 for Ts seconds, as shown in FIG. 3. Since the reception circuit 31 is in an inactive state during this period, the power consumed by the reception circuit 31 greatly reduces.

Radio signals are transmitted from the transmitting section 1 at intervals of Tj seconds. Since the time period Ts during which the reception circuit 31 is stopped by the reception control signal Ss is shorter than Tj seconds, there is no influence on reception of the next radio signal to be transmitted upon lapse of Tj seconds. In an initial state in which no radio signal is received, since a reception control signal Ss is not output, the reception circuit 31 is in a normal operation state, and there is no possibility that the first radio signal cannot be received. Even if the reception circuit 31 receives noise or an irrelevant signal and outputs a detection signal Sk, since the output signal is not correct data, the data decoding circuit 32 cannot properly decode it. For this reason, a decoding end signal Se is not output, and the operation of the reception circuit 31 is not stopped by the reception control signal Ss.

As described above, in the normal operation state, the reception circuit 31 is stopped for Ts seconds of the larger Tj seconds. The apparent power consumption of the reception circuit 31 is therefore represented by Ts/Tj. In the receiving section 2, the reception circuit 31, which is the only analog circuit, consumes the most power. If, therefore, the apparent power consumption of the reception circuit 31 is reduced, the power consumption of the receiving section 2 can be greatly reduced. If the second information data Sm$_1$ and the ID code data Sm$_2$ are added to a radio signal, in addition to the electrocardiographic interval data Sn, the reception time is prolonged by the data lengths of the second information data Sm$_1$ and the ID code data Sm$_2$. A considerable increase in power consumption can be prevented by properly setting the relationship between transmission intervals Tj and the data length.

Figure 4:
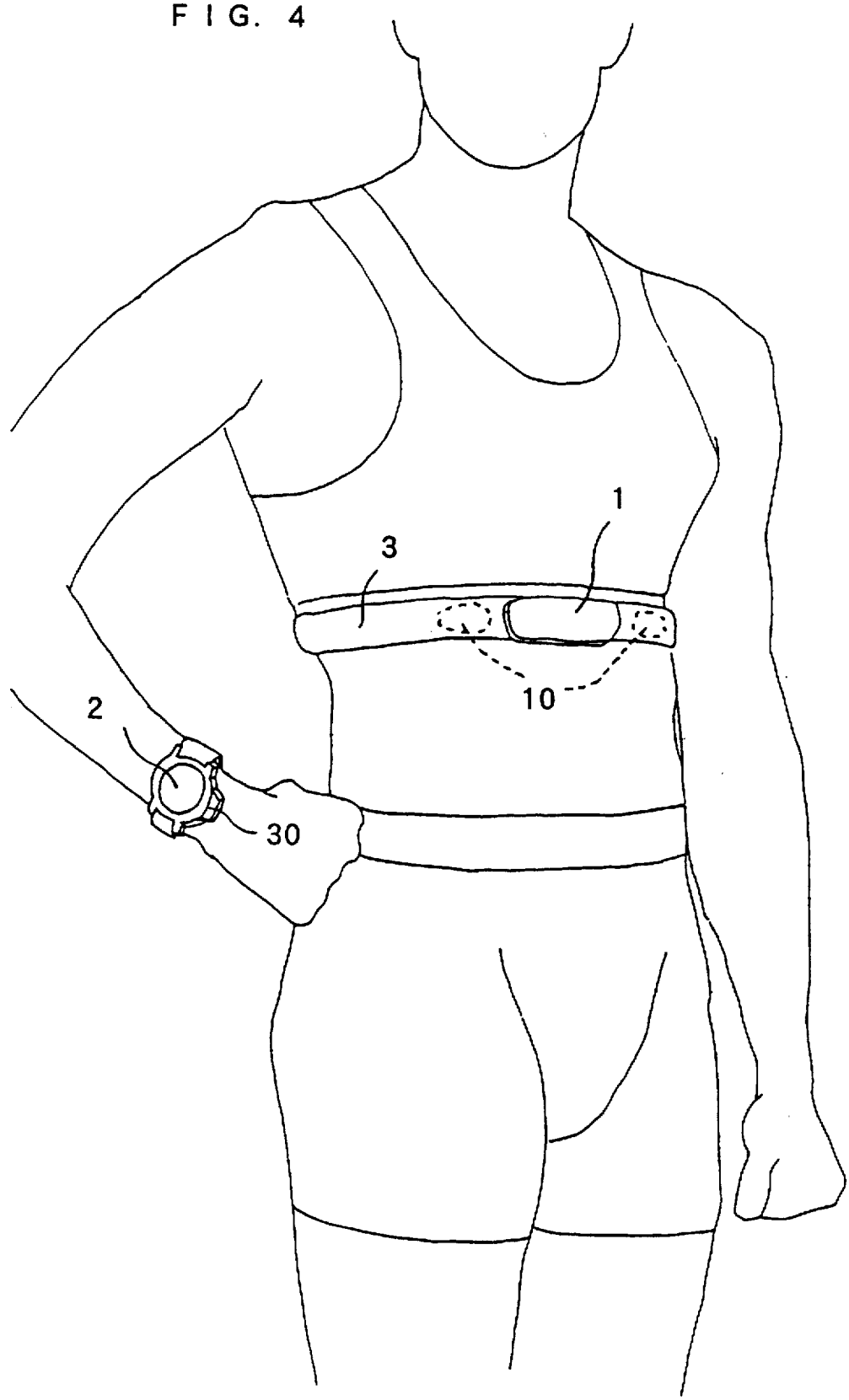
FIG. 4 is a view showing how the cardiotachometer according to the embodiment of the present invention is mounted.

FIG. 4 shows how the cardiotachometer according to the embodiment of the present invention is mounted.

The transmitting section 1 is fixed on the chest of the user with a belt 3 such that one of the electrodes 10 is located near the heart. For example, the electrode 10 is made of conductive rubber, and is brought into direct contact with the skin. The receiving section 2 also has a timepiece function and is worn on the wrist, similar to a general wristwatch.

Figure 5:
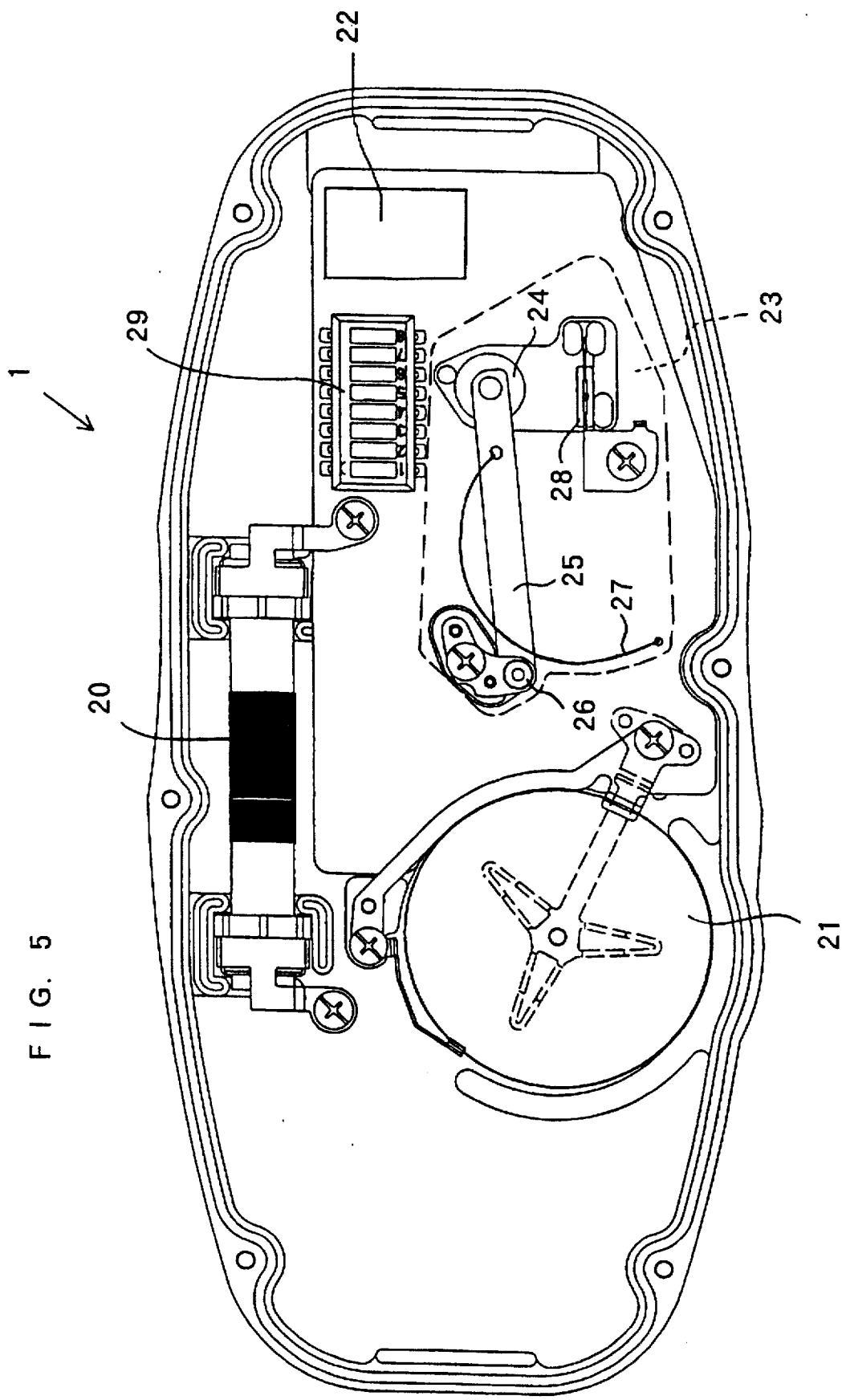
FIG. 5 is a view showing the interior of the transmitting section of the cardiotachometer according to the embodiment of the present invention.

FIG. 5 is an external view showing the transmitting section of the cardiotachometer according to the embodiment of the present invention. Referring to FIG. 5, the cover is removed to show the interior of the transmitting section.

Reference numeral 20 denotes an antenna for transmitting a radio signal to the receiving section 2; 21, a battery as a power supply; 22, an IC which realizes each processing; 23, a walk detection mechanism as an example of the acceleration sensor 18 in FIG. 1; and 29, a DIP switch as an example of the ID code generating means 19 in FIG. 1.

In the transmitting section 1, a walk detection mechanism 23 has a weight 24, an arm 25, a fulcrum 26, a spring 27, and a contact 28. In a normal state, the arm 25 and the weight 24 are lifted with the force of the spring 27, and the weight 24 is not in contact with the contact 28. When the user having the transmitting section 1 mounted thereon walks, the weight 24 swings about the fulcrum 26 upon vertical movement of the user which occurs as he/she walks, and the weight 24 is brought into contact with the contact 28 for every step of the walk. For example, the weight 24, the contact 28, and the like are made of conductors, so a current flows when the weight 24 is brought into contact with the contact 28. Every step of the walk can therefore be detected.

In the description made with reference to FIGS. 1 and 2, second information is the walking pitch. However, the second information is not limited to this in the present invention. For example, as second information, the receiving section 2 may be notified of a voltage drop in the battery 21 or the total number of steps detected by the walk detection mechanism 23 from the transmitting section 1.

The DIP switch 29 in the transmitting section 1 can generate various ID codes by changing the setting. An ID code identical to an ID code set by the DIP switch 29 is stored in the ID code storage means 38 of the receiving section 2.

Figure 6:
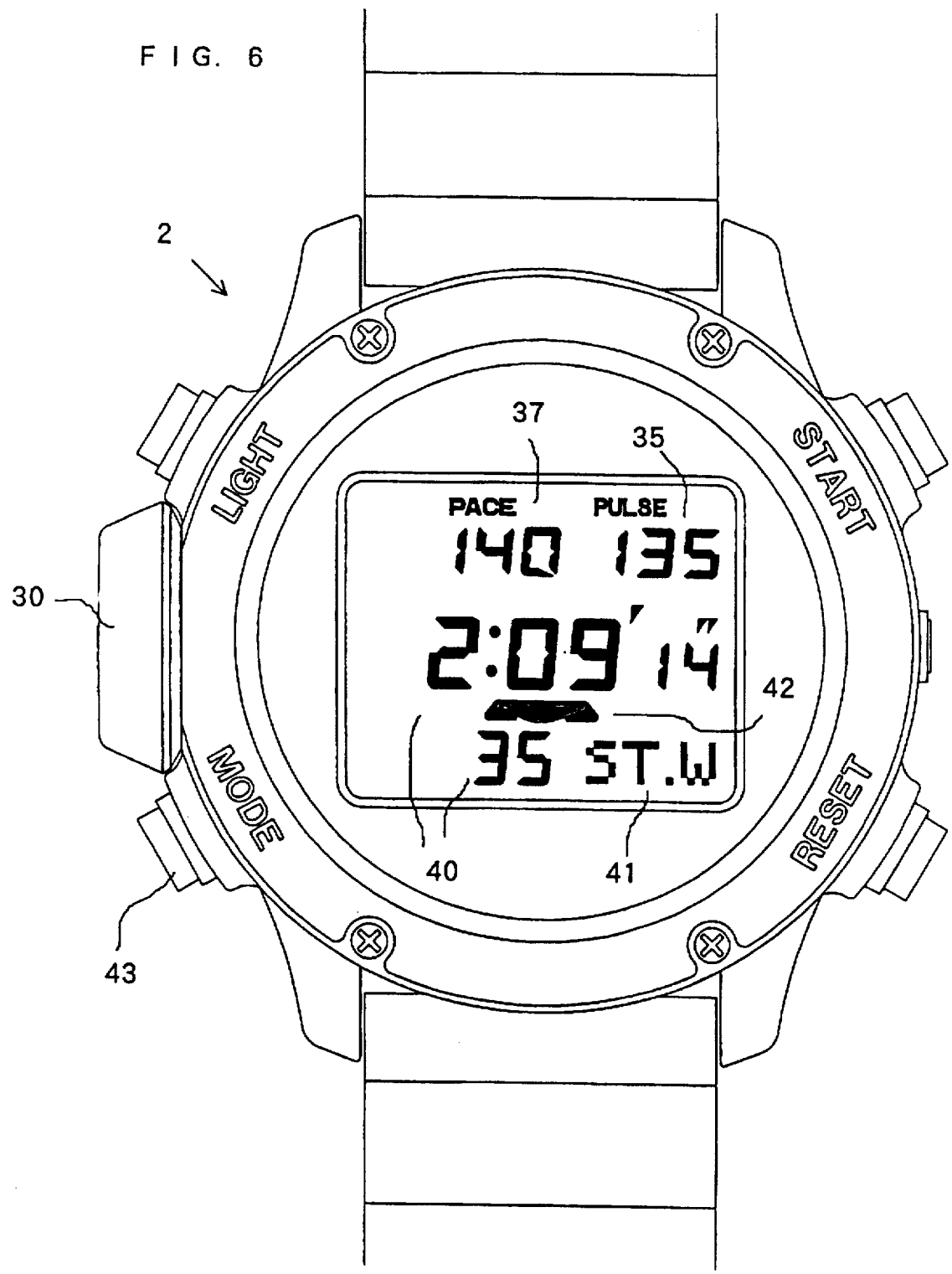
FIG. 6 is an external view showing the receiving section of the cardiotachometer according to the embodiment of the present invention.

FIG. 6 is an external view showing the receiving section of the cardiotachometer according to the embodiment of the present invention.

The receiving section 2 is of a wristwatch type, and has a timepiece function. The antenna 30 for receiving a radio signal from the transmitting section 1 is mounted on a side portion of the receiving section 2. The upper surface of the receiving section 2 has the display section 35 for displaying the heart rate per minute, the second information display section 37 for displaying, e.g., the number of steps per minute, a time display section 40 for displaying the time measured, a mode display section 41 for displaying the current mode which can be changed by depressing a mode change button 43, and a reception state display section 42 for displaying the reception state from the transmitting section 1.

Referring to FIG. 6, the display section 35 displays "135" as the heart rate per minute; the second information display section 37 displays "140" as the number of steps per minute or pace; the mode display section 41 displays the stop watch mode; and the time display section 40 displays "2 hours, 9 minutes, 14.35 seconds" as the time measured by the stop watch. When the mark is displayed on the reception state display section 42 as shown in FIG. 6, it indicates that the receiving section is currently in the reception state.

When the mode change button 43 is depressed, for example, the information displayed on the second information display section 37 can be changed from the number of steps per minute to the total number of steps. In addition, the information displayed on the time display section 40 can be changed from the time measured by the stop watch to the current time.

When a warning about a voltage drop in the battery 21 in the transmitting section 1 is received as second information from the transmitting section 1, the mode display section 41 is controlled to alternately display the current mode "ST. w" and "BT. t" indicating a battery voltage drop on the transmitting section 1. When a power supply voltage drop in the receiving section 2 is detected, the mode display section 41 is controlled to alternately display the current mode "ST. w" and "BT. w" indicating a battery voltage drop on the receiving section 2.

In the description made with reference to FIGS. 1 and 2, the ID code comparison/determination circuit 39 compares the ID code data $Sm_2$ decoded by the data decoding circuit 32 with the electrical signal $Sa_2$ output from the ID code storage means 38, and determines and outputs the result signal Sb to the calculation circuit 34 and the second information calculation circuit 36. However, the present invention is not limited to this configuration. For example, the signal to be transmitted from the transmitting section 1 to the receiving section 2 may have a format like the one shown in FIG. 7 to perform more accurate comparison/determination. An operation in this case will be described below.

The conversion means 14a of the serial data creating circuit 14 in FIG. 1 links ID code data $Sl_2$, electrocardiographic interval data Sd, second information data Sc, and ID code data $Sl_2$ in the order named to generate a serial data signal Sr.

The data separation means 32a of the data decoding circuit 32 in FIG. 2 separates the reception signal Sj into ID code data $Sm_2$, electrocardiographic interval data Sn, second information data $Sm_1$, and ID code data $Sm_2$. Thereafter, the ID code comparison/determination circuit 39 compares the ID code data $Sm_2$ separated from the reception signal Sj with the electrical signal $Sa_2$ output from the ID code storage means 38. The ID code comparison/determination circuit 39 also compares the ID code data $Sm_2$ appended to the start portion of the reception signal Sj with the ID code data $Sm_2$ appended to the end portion of the reception signal Sj, and determines and outputs a binary signal Sb as the result to the calculation circuit 34 and the second information calculation circuit 36.

When the binary signal Sb indicates coincidence as the result, the calculation circuit 34 and the second information calculation circuit 36 perform calculation and display, as described above. If, however, the binary signal Sb indicates noncoincidence as the result, no calculation is performed, and the previous calculation results are kept displayed on the display section 35 and the second information display section 37. With this operation, the reliability of the reception signal Sj can be improved.

As described above, according to the present invention, although heartbeat data is transmitted at predetermined intervals of Tj seconds, the power consumption of the transmitting section 1 can be greatly reduced by adjusting the time Tj (seconds) to a proper value. In addition, the power consumption of the reception circuit 31 of the receiving section 2 can be set to Ts/Tj by controlling the reception circuit 31 of the receiving section 2 through the reception control circuit 33. Therefore, the total power consumption of the transmitting section 1 and the receiving section 2 can be greatly reduced, and the service life of each battery can be prolonged by reducing the battery power consumption, thereby reducing the frequency of battery replacement. Even if the receiving section 2 is incorporated in a compact electronic device such as a wristwatch, the section can be driven for a long period of time with a small battery. By reducing the frequency of battery replacement, a more convenient cardiotachometer can be provided.

In addition, according to the present invention, the transmission side has the function of detecting second information data other than electrocardiographic interval data and the function of linking two data into serial data, whereas the reception side has the function of decoding serial data into electrocardiographic interval data and second information data. The calculation circuits are capable of processing the respective data and the display sections. With this arrangement, the cardiotachometer has additional functions other than the heartbeat measurement function. A functional improvement on the cardiotachometer can therefore be attained.

Furthermore, according to the present invention, the transmission side has the ID code setting function and the function of linking electrocardiographic interval data to ID code data into serial data, whereas the reception side has the function of decoding serial data into electrocardiographic interval data and ID code data, the ID code storage function, and the function of comparing/determining a transmitted ID code with a stored ID code. With this arrangement, the cardiotachometer has the function of preventing erroneous reception and calculation of heartbeat data owing to interference or the like. Therefore, the reliability of reception performed by the cardiotachometer can be improved.

The present invention is not limited to the integration of the receiving section of the cardiotachometer and the timepiece function. For example, with an altimeter function, an electronic device can be provided, which allows a user to see the altitude and his/her heart rate at a glance in mountain climbing.

We claim:

1. A cardiotachometer for processing electrocardiographic signals on cardio-condition of the heart of a human body obtained from a pair of electrodes mounted near the heart of a human body, the cardiotachometer comprising:

a transmitting section which includes:

a detection circuit for detecting the electrocardiographic signals and generating detection signals with generation intervals, an interval data creating circuit coupled with the detection circuit for counting the generation intervals of the detection signals with signals of a preset period and generating interval data, ID code generating means for creating a transmitted ID code for identification, a serial data creating circuit coupled to the interval data creating circuit and ID code generating means for linking the interval data with the transmitted ID code to generate a serial data signal, and a transmission circuit coupled to the serial data creating circuit for modulating the serial data signal and transmitting the modulated serial data signal as a radio signal; and a receiving section which includes:

a reception circuit for receiving and demodulating the radio signal from the transmitting section and generating a reception signal, a data decoding circuit coupled to the reception circuit for decoding the reception signal and generating the serial data signal, data separation means coupled to the data decoding circuit for separating the interval data and the transmitted ID code from the serial data signal, ID code storage means for storing a stored ID code, ID code comparison/determination means coupled to the data separation means and the ID code storage means for comparing the transmitted ID code and the stored ID code and determining a comparison signal indicating whether the separated interval data are reliable, a calculation circuit coupled to the data separation means and ID code comparison/determination means for receiving the interval data and calculating a heart rate from the interval data if the comparison signal indicates the separated interval data are reliable, and a display section for displaying the heart rate.

2. A cardiotachometer according to claim 1, wherein the cardiotachometer is connected to a battery as power supply.

3. A cardiotachometer according to claim 1, wherein the radio signal from the transmission circuit is an intermittent radio signal to be transmitted at predetermined intervals.

4. A cardiotachometer according to claim 1, wherein the interval data has a start portion and an end portion, the serial data creating circuit links the interval data with the transmitted ID code to generate the serial data signal by appending the transmitted ID code to the start and end portions of the interval data to convert the serial data into a serial signal and generate the serial data signal, and the ID code comparison/determination means compares the transmitted ID code appended to the start portion of the interval data with the transmitted ID code appended to the end portion of the interval data, and determines on the basis of the comparison result whether the separated interval data are reliable.

5. A cardiotachometer according to claim 1, wherein the transmitting section further comprises:

second information detection means for detecting second information from the pair of electrodes and generating a second information detection signal, and a second information data creating circuit coupled to the second information detection means for creating second information data on the basis of the second information detection signal, the serial data creating circuit further coupled to the second information data creating circuit for linking the interval data and the transmitted ID code to the second information data to generate the serial data signal, the data separation means of the receiving section separating the second information data, the interval data, and the transmitted ID code from the serial data signal, and the receiving section further comprises:

second information calculation means for performing arithmetic processing of the separated second information data which can be displayed by the display section.

6. A cardiotachometer according to claim 5, wherein the second information detection means comprises a pedometer having walk detection means for detecting number-of-steps data, and the second information data comprises the number-of-steps data.

7. A cardiotachometer according to claim 5, wherein the second information detection means comprises walk detection means for detecting a walk and generating walk detection signals, and a walking interval data creating circuit which includes signals of a preset period and uses the signals to count generation intervals of the walk detection signals to generate walking interval data, and the second information data includes the walking interval data.

8. A cardiotachometer according to claim 5, wherein the cardiotachometer is connected to a battery as power supply, the second information detection means comprises a voltage detection circuit for the battery, and the second information data include battery voltage drop warning data of the battery.

* * * * *